US 8,777,874 B2

(12) United States Patent
Zhang et al.

(10) Patent No.: US 8,777,874 B2
(45) Date of Patent: Jul. 15, 2014

(54) ACOUSTIC BASED COUGH DETECTION

(75) Inventors: Xusheng Zhang, Shoreview, MN (US);
Vinod Sharma, Maple Grove, MN (US);
Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 300 days.

(21) Appl. No.: 13/114,838

(22) Filed: May 24, 2011

(65) Prior Publication Data
US 2012/0302898 A1 Nov. 29, 2012

(51) Int. Cl.
*A61B 7/00* (2006.01)

(52) U.S. Cl.
USPC .......................................... 600/586; 600/484

(58) Field of Classification Search
USPC ................................................... 600/484, 586
See application file for complete search history.

(56) References Cited

U.S. PATENT DOCUMENTS

| 4,374,382 | A | 2/1983 | Markowitz |
|---|---|---|---|
| 5,117,824 | A | 6/1992 | Keimel et al. |
| 5,545,186 | A | 8/1996 | Olson et al. |
| 5,755,736 | A | 5/1998 | Gillberg et al. |
| 6,393,316 | B1 | 5/2002 | Gillberg et al. |
| 6,449,508 | B1 | 9/2002 | Sheldon et al. |
| 6,643,548 | B1 | 11/2003 | Mai et al. |
| 7,123,962 | B2 | 10/2006 | Siejko et al. |
| 7,139,609 | B1 | 11/2006 | Min et al. |
| 7,209,786 | B2 | 4/2007 | Brockway et al. |
| 7,212,849 | B2 | 5/2007 | Zhang et al. |
| 7,248,923 | B2 | 7/2007 | Maile et al. |
| 7,343,915 | B2 * | 3/2008 | Addington et al. ........ 128/203.12 |
| 7,460,909 | B1 | 12/2008 | Koh et al. |
| 7,689,283 | B1 | 3/2010 | Schecter |
| 7,787,946 | B2 | 8/2010 | Stahmann et al. |
| 2004/0220636 | A1 | 11/2004 | Burnes |
| 2005/0080461 | A1 * | 4/2005 | Stahmann et al. ............... 607/17 |
| 2007/0049977 | A1 * | 3/2007 | Von Arx et al. ................... 607/9 |
| 2007/0123943 | A1 | 5/2007 | Patangay et al. |
| 2007/0142866 | A1 | 6/2007 | Li et al. |
| 2007/0150014 | A1 | 6/2007 | Kramer et al. |
| 2007/0150017 | A1 | 6/2007 | Salo |
| 2008/0051839 | A1 * | 2/2008 | Libbus et al. ...................... 607/2 |
| 2008/0082018 | A1 * | 4/2008 | Sackner et al. ............... 600/538 |
| 2008/0103399 | A1 | 5/2008 | Patangay et al. |
| 2008/0195168 | A1 | 8/2008 | Arand et al. |
| 2008/0234594 | A1 | 9/2008 | Brooks et al. |
| 2008/0275349 | A1 * | 11/2008 | Halperin et al. ............... 600/484 |
| 2008/0294213 | A1 | 11/2008 | Holmstrom et al. |
| 2009/0048640 | A1 | 2/2009 | Bauer et al. |
| 2009/0131999 | A1 | 5/2009 | Li et al. |

(Continued)

OTHER PUBLICATIONS

U.S. Appl. No. 13/111,260, by Zhang et al., filed May 19, 2011.

(Continued)

*Primary Examiner* — Navin Natnithithadha
*Assistant Examiner* — Etsub Berhanu
(74) *Attorney, Agent, or Firm* — Michael C. Soldner

(57) ABSTRACT

The present disclosure is directed to the detection of coughs and coughing episodes using acoustic signals. In various examples, an implantable medical device processes an acoustic signal obtained from an acoustic sensor to determine whether a patient has coughed. In some examples, the implantable medical device also performs a cough severity assessment. In some examples, the cough severity assessment may include a determination of the depth of the cough, the duration of the coughing episode, or whether the cough was wet or dry.

29 Claims, 11 Drawing Sheets

(56) References Cited

U.S. PATENT DOCUMENTS

| | | | |
|---|---|---|---|
| 2009/0216138 A1 | 8/2009 | Arand | |
| 2009/0254139 A1 | 10/2009 | Bjorling | |
| 2010/0023078 A1 | 1/2010 | Dong et al. | |
| 2010/0069768 A1 | 3/2010 | Min et al. | |
| 2010/0073170 A1 | 3/2010 | Siejko et al. | |
| 2010/0185109 A1 | 7/2010 | Zhang et al. | |
| 2010/0198308 A1 | 8/2010 | Zhou et al. | |
| 2010/0312130 A1* | 12/2010 | Zhang et al. | 600/508 |
| 2010/0331903 A1 | 12/2010 | Zhang et al. | |
| 2011/0015535 A1 | 1/2011 | Lange et al. | |
| 2011/0015703 A1 | 1/2011 | Ternes et al. | |
| 2011/0015704 A1 | 1/2011 | Ternes et al. | |
| 2011/0087079 A1* | 4/2011 | Aarts | 600/300 |

OTHER PUBLICATIONS

Stec et al., "Premature ventricular complex-induced chronic cough and cough syncope," Eur Respir J. 2007:30 (2):391-394.

Toggweiler et al., "Visualizing Pacemaker-Induced Phrenic Nerve Stimulation with Acoustic Cardiography," PACE 2007; 30:806-807.

Zuber et al., "Detection and Hemodynamic Significance of Cardiac Pacemaker-Induced Phrenic Nerve Stimulation," Congest Heart Fail. 2010:16:147-152.

Stahlberg et al., "Cardiac output response to changes of the atrioventricular delay in different body positions and during exercise in patients receiving cardiac resynchronization therapy," Europace (2009) 11: 1160-1167.

Zuber et al., "Systolic Dysfunction: Correlation of Acoustic Cardiography With Doppler Echocardiography," CHF. 2006; 12(4 supple 1): 14-18.

Auricchio et al., "Effect of Pacing Chamber and Atrioventricular Delay on Acute Systolic Function of Paced Patients With Congestive Heart Failure," Circulation 1999;99:2993-3001.

Baker, II et al., "Acute Evaluation of Programmer-Guided AV/PV and VV Delay Optimization Comparing an IEGM Method and Echocardiogram for Cardiac Resynchronization Therapy in Heart Failure Patients and Dual-Chamber ICD Implants," J Cardiovasc Electrophysiol, vol. 18, pp. 1-7, Jan. 2007.

Gold et al., "A Prospective Comparison of AV Delay Programming Methods for Hemodynamic Optimization during Cardiac Resynchronization Therapy," J Cardiovasc Electrophysiol, vol. 18, pp. 1-7, May 2007.

Gras et al., "Optimization of AV and VV Delays in the Real-World CRT Patient Population: An International Survey on Current Clinical Practice," PACE 2009;32:S236-23.

O'Donnell et al., "Long-Term Variations in Optimal Programming of Cardiac Resynchronization Therapy Devices," PACE 2005;28:S24-26.

Erne, "Beyond auscultation-acoustic cardiography in the diagnosis and assessment of cardiac disease," Swiss Med Wkly 2008;138(31-32):439-452.

U.S. Appl. No. 13/474,041, by Zhang et al., filed May 17, 2012.
U.S. Appl. No. 13/474,074, by Zhang et al., filed May 17, 2012.
U.S. Appl. No. 13/360,149, by Anderson et al., filed Jan. 27, 2012.

* cited by examiner

ACOUSTIC BASED COUGH DETECTION

TECHNICAL FIELD

The disclosure relates to patient monitoring and, more particularly, cough detection.

BACKGROUND

A wide variety of implantable medical devices for delivering a therapy or monitoring a physiologic condition have been clinically implanted or proposed for clinical implantation in patients. For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation. In some cases, such an implantable medical device (IMD) may sense for intrinsic depolarizations of the heart, and control the delivery of such signals to the heart based on the sensing. When an abnormal rhythm is detected, which may be bradycardia, tachycardia or fibrillation, an appropriate electrical signal or signals may be delivered to restore the normal rhythm. For example, in some cases, an implantable medical device may deliver pacing, cardioversion or defibrillation signals to the heart of the patient upon detecting ventricular tachycardia, and deliver defibrillation electrical signals to a patient's heart upon detecting ventricular fibrillation. Pacing signals typically have a lower energy than the cardioversion or defibrillation signals.

In some cases, an IMD device includes sensors for detecting heart sounds signals in addition to electrical signals. As described in Published U.S. Patent Application 2010/0331903 to Zhang et al. entitled "HEART SOUND SENSING TO REDUCE INAPPROPRIATE TACHYARRHYTHMIA THERAPY", incorporated herein by reference in its entirety, heart sounds signals are detected and used to determine whether the heart sounds are normal or abnormal. The heart sounds may also be used to confirm or reject an indication that therapy may be needed based on electrical signals.

Heart failure is a condition affecting thousands of people worldwide. Essentially, congestive heart failure occurs when the heart is unable to pump blood at an adequate rate in response to the filling pressure. A worsening heart failure condition may result in symptoms such as congestion in the tissue, peripheral edema, pulmonary edema, and shortness of breath, and coughing. When heart failure is severe, it can even lead to patient death.

SUMMARY

In general, the present disclosure is directed to detection of a cough using an implanted acoustic sensor. In some examples, the cough detection can be used to monitor heart failure, confirm ventricular tachycardia (VT) or ventricular fibrillation (VF), or to update an assessment of the risk of VT or VF. In various examples, the determination of whether a cough occurred is based at least in part on both an acoustic signal and a patient activity signal. In some examples, the patient activity signal is an activity level count. The acoustic and patient activity signals may also be used to determine various features of the cough. For example, a severity assessment of the cough may be performed.

In one example, the disclosure is directed to a method in which a device receives an acoustic signal from an acoustic sensor implanted in a patient, receives a patient activity signal form an activity sensor implanted in the patient, analyzes the acoustic signal in combination with the patient activity signal, and determines whether a cough has occurred based on the analysis of the acoustic signal in combination with the patient activity signal.

In another example, the disclosure is directed to a system including an acoustic sensor configured to detect an acoustic signal, an activity sensor configured to detect a patient activity signal, a cough analyzer configured to receive an acoustic signal from the acoustic sensor, receive a patient activity signal form the activity sensor and analyze the acoustic signal in combination with the patient activity signal, and a processor configured to determine whether a cough has occurred based on the analysis of the acoustic signal in combination with the patient activity signal.

The details of one or more examples are set forth in the accompanying drawings and the description below. Other features, objects, and advantages will be apparent from the description and drawings, and from the claims.

DETAILED DESCRIPTION

Figure 1:
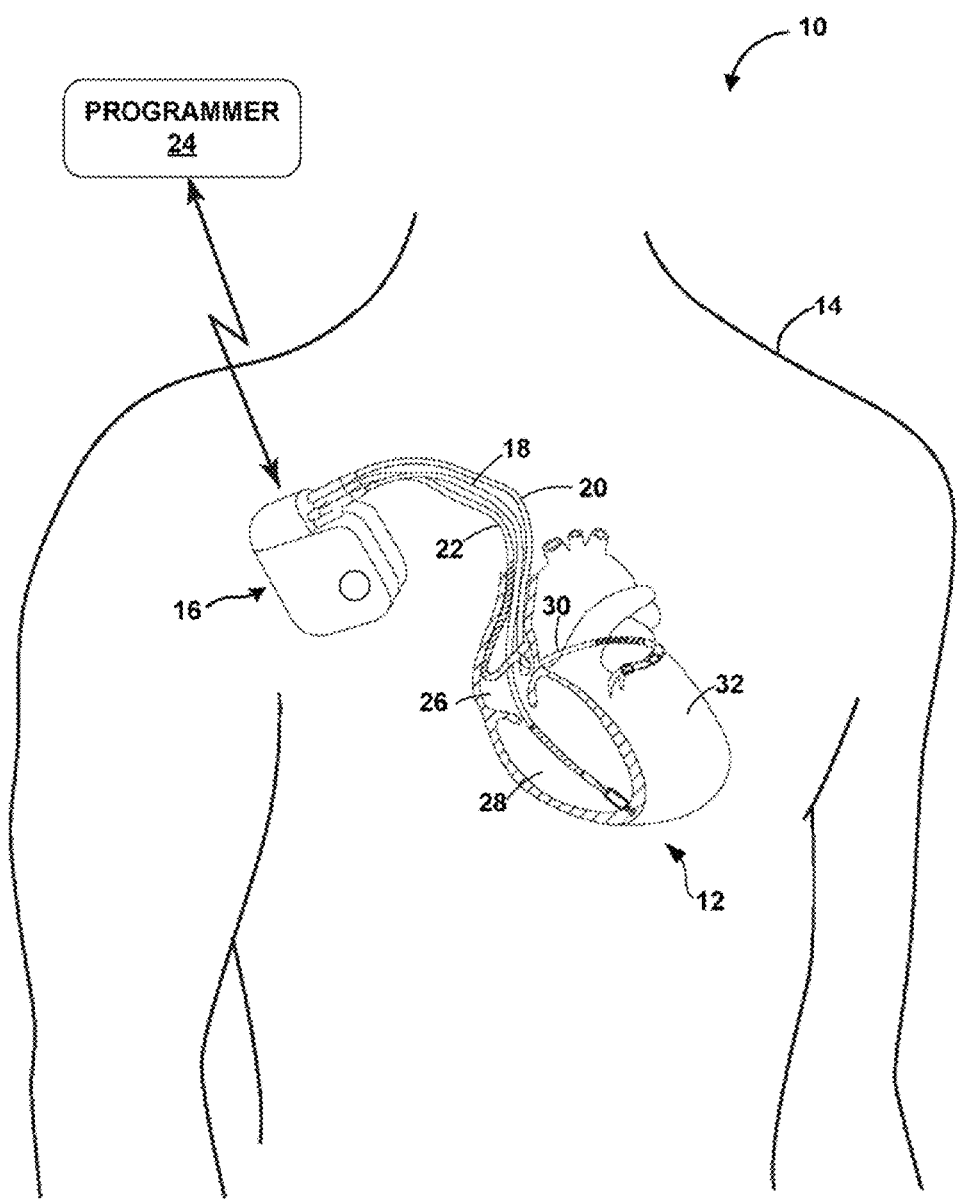
FIG. 1 is a conceptual diagram illustrating an example system that detects acoustic signals for cough detection, consistent with an example of the present disclosure.

Coughing is a significant symptom in Heart Failure (HF) patients that may indicate a worsening of lung congestion and decline in overall health status of an HF patient. The presence of a cough may also be correlated to a higher incidence of premature ventricular contractions (PVCs). As the extent of PVCs may be correlated to the risk of arrhythmias, the presence of a cough may be useful in predicting a patient's risk for arrhythmias.

Heart failure is marked by a drop in the ability of the heart to pump blood through the circulatory system. One common result of the drop in pumping ability is lung congestion, which in turn leads to increased incidents of coughing as the patient tries to clear the airway and bronchial passages. Coughs associated with heart failure may exhibit a wide range of characteristics. For example, a patient may experience a wet, frothy cough that may be tinged pink with blood. In some examples, a patient may experience a dry, hacking cough that does not expel mucous. Some patients may experience both wet and dry coughs at different times. In some examples, coughing spells may be accompanied by a bubbling feeling or a whistling sound in the patient's lungs. In some examples, heavy wheezing and/or labored breathing may also company coughing spells.

In some examples, coughing may be detected by one or both of an acoustic sensor and an activity sensor inside an IMD. Acoustic signals during coughing demonstrate different waveforms with distinct morphology, frequency, duration, timing, and patterns. These characteristics may be discriminated from the other sounds, such as noise and artifacts in an acoustic signal caused by other motions. In some examples, the activity sensor senses the movement of the chest of the patient associated with coughing. In some examples, an activity level count is determined from an accelerometer signal. In some examples, a weighted activity level count is acquired over an interval, e.g., an approximately one second interval, which is updated periodically, e.g., approximately every half second. In some examples, the activity count can be calculated over a one second interval and updated at a one second interval.

In some examples, an acoustic sensor may detect a heart sounds signal. As used herein, the term heart sound refers to a feature of the heart sounds signal, such as the S1, S2, S3 or S4 heart sounds. It may also refer to a feature of the heart sounds signal that results from other physiological events, such as a cough, or phrenic nerve stimulation resulting in activation of the diaphragm. There may be multiple heart sounds, e.g., each of an S1, S2, S3 and S4 heart sound, for any given cardiac cycle or heartbeat. A cardiac device detecting heart sounds may, for example, confirm that a cardiac rhythm is within a normal range based on the characteristics of the heart sounds detected and the presence or absence of certain heart sounds.

In some examples below the signals use below to detect the presence of a cough are referred to as a heart sounds signal and an activity signal. However, one of skill in the art would understand that the heart sounds signal is derived from an acoustic sensor, and does not necessarily include heart sounds S1-S4. For example, depending on the placement of the acoustic sensor, the presence of heart sounds S1-S4 may be minimal in the overall signal.

FIG. 1 is a conceptual diagram illustrating an example system 10 that detects acoustic signals and, based on the acoustic signals, detects the presence and, in some examples, the severity of a cough in a patient 14. In some examples, system 10 also monitors patient activity, and detects the presence of cough based on a patient activity signal and the acoustic signals. System 10 may also monitor cardiac electrical activity and, in some examples, provides cardiac pacing therapy or other cardiac therapies. In addition, system 10 may monitor the effectiveness of the therapy being provided as well as possible side effects. For example, system 10 may monitor for phrenic nerve stimulation.

System 10 includes implantable medical device (IMD) 16, which is connected to leads 18, 20, and 22 and is communicatively coupled to a programmer 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16, the therapy may be pacing, cardioversion and/or defibrillation pulses. IMD 16 also includes, or is coupled to via one or more leads 18, 20 and 22, one or acoustic sensors (not shown in FIG. 1). Inn some examples, at least one of the acoustic sensors is a heart sounds sensor. IMD may similarly include or be coupled to other sensors, such as one or more accelerometers, for detecting other physiological parameters of patient 14, such as activity or posture.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. A user may also interact with programmer 24 to program IMD 16, e.g., select values for operational parameters of the IMD.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

Figure 2:
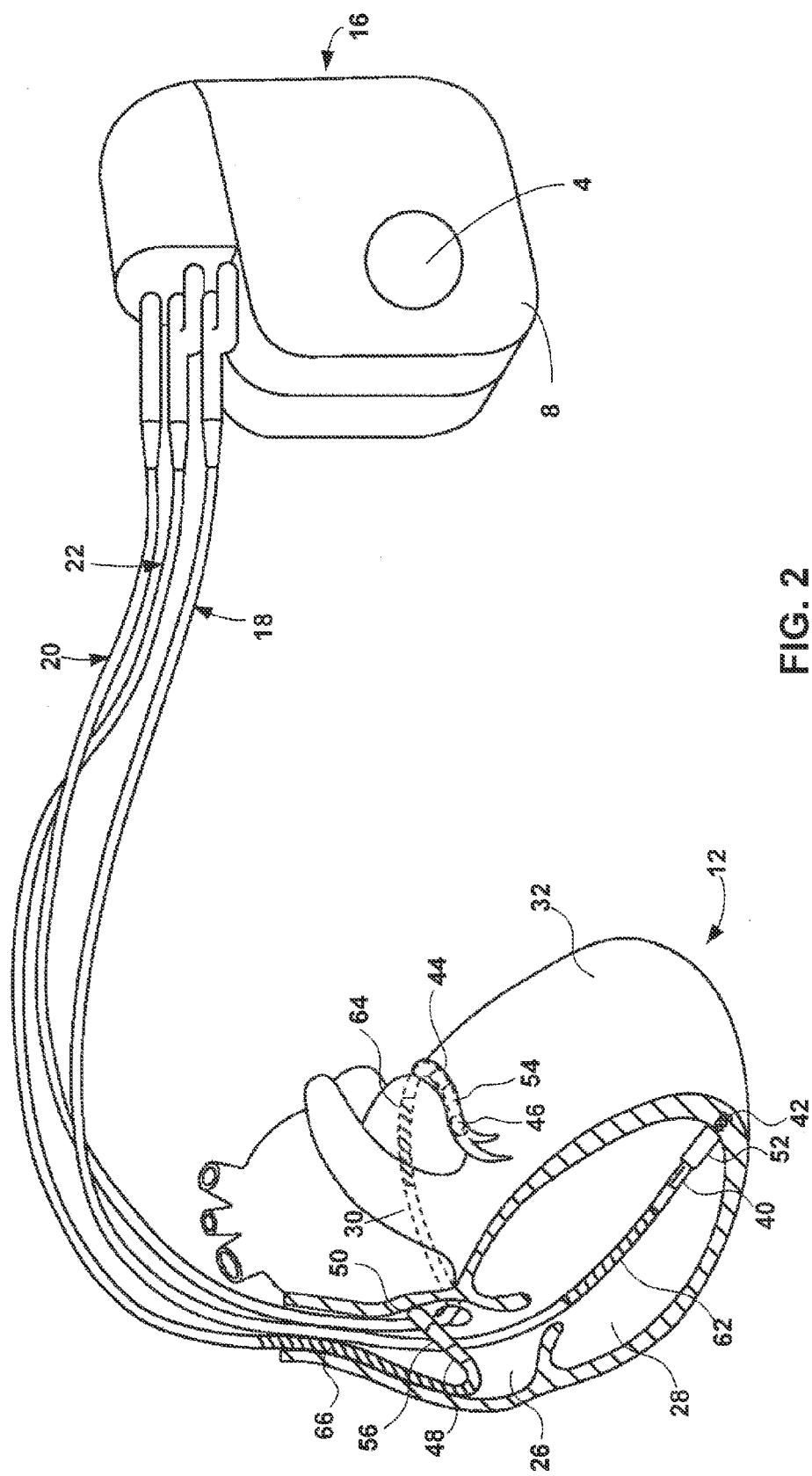
FIG. 2 is a conceptual diagram illustrating the implantable medical device (IMD) and leads of the system shown in FIG.1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative embodiments, not shown in FIG. 2, one or more of leads 18, 20 and 22, e.g., left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes 40, 42, 44, 46, 48, 50, 62, 64 and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioverison and defibrillation pulses, as well as a sensing module for sensing electrical signals attendant to the depolarization and repolarization of heart 12. Housing 8 may also enclose an acoustic sensor that generates an electrical signal based on sensed acoustic vibrations. In some examples the acoustic sensor is a heart sounds sensor that generates an electrical signal based on sensed heart sounds. The acoustic sensor may be enclosed within housing 8. Alternatively, the acoustic sensor may be integrally formed with an outer surface of housing 8, carried on a lead coupled to IMD 16, such as one or more leads 18, 20 and 22, or be a remote sensor that wirelessly communicates with IMD 16, programmer 24 or any other device described herein.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within the heart. In some examples, system 10 may include an additional lead that carries an acoustic sensor positioned such that signals generated by the acoustic sensor include respiratory sounds in response to a cough or diaphragm movement.

Furthermore, in some examples, IMD 16 need not be coupled to any leads, need not provide electrical stimulation or other therapy, and/or need not sense electrical cardiac signals. In some examples, the techniques described herein may be implemented in a leadless monitoring device, such as a Reveal® insertable monitor available from Medtronic, Inc. of Minneapolis, Minn. Such a device may be configured to include an acoustic sensor and, in some examples, an activity sensor, and provide the functionality described herein with respect to IMD 16.

Figure 3:
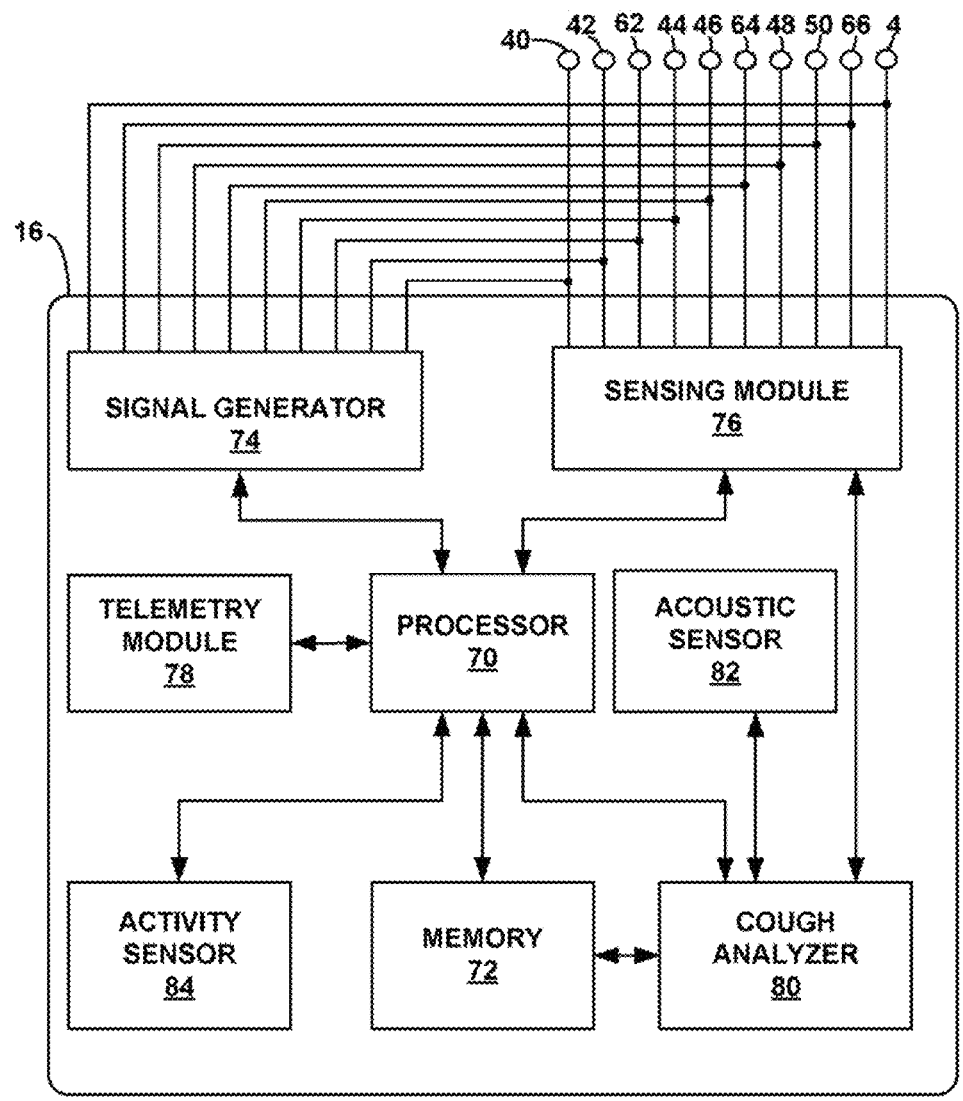
FIG. 3 is a block diagram illustrating an example configuration of the IMD of FIG. 1.

FIG. 3 is a block diagram illustrating an example configuration of IMD 16. In the illustrated example, IMD 16 includes a processor 70, memory 72, signal generator 74, sensing module 76, telemetry module 78, cough analyzer 80, acoustic sensor 82, and activity sensor 84. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs or parameters.

Signal generator 74 is configured to generate and deliver electrical stimulation therapy to patient 14. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 may analyze the digitized version of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 70 in some examples. For example, EGM morphology may be considered in addition to or instead of interval length for detecting tachyarrhythmias.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, processor 70 may mistakenly classify the patient's heart rhythm as a treatable tachyarrhythmia, e.g., as a result of a noisy EGM.

IMD 16 also includes acoustic sensor 82, cough analyzer 80 and activity sensor 84. Acoustic sensor 82 generates an electrical signal based on sound or vibration, e.g., sensed heart sounds of patient 14, and may be implemented as a piezoelectric sensor, a microphone, an accelerometer, or other type of acoustical sensor. In some examples, acoustic sensor 82 may comprise more than one sensor. For example, acoustic sensor 82 may include multiple accelerometer devices. Activity sensor 84 may also comprise one or more accelerometers. Information obtained from acoustic sensor 82 and activity sensor 84 may be used to provide a risk assessment with regard to worsening heart failure or ventricular tachycardia and/or fibrillation. In some examples, signals from the acoustic sensor 82 and activity sensor 84 are provided to cough analyzer 80 and, based on information extracted from the signals, coughs may be detected.

In the illustrated example of FIG. 3, acoustic sensor 82 is enclosed within housing 8 of IMD 16. In some examples, acoustic sensor 82 may be formed integrally with an outer surface of housing 8. For example, acoustic sensor 82 may be a piezoelectric sensor attached to the outer surface of housing 8. In some examples, acoustic sensor 82 is located on a lead that is coupled to IMD 16 or may be implemented in a remote sensor that wirelessly communicates with IMD 16 via telemetry module 78. In any case, acoustic sensor 82 is electrically or wirelessly coupled to circuitry contained within housing 8 of IMD 16.

Cough analyzer 80 receives the electrical signal generated by acoustic sensor 82. In some examples, cough analyzer 80 processes the sensor signal to detect coughs and determine whether specified events occurred during a given time period.

In some examples, cough analyzer 80 processes the acoustic signal to generate an envelope signal, applies an algorithm that uses an adaptively decaying threshold to detect events within the envelope signal, extracts event features from the detected events, and determines whether a cough has occurred based on event features. In some examples the detected cough features are compared to values for each feature stored in memory 72. A determination of the severity or type of cough may be made based on the deviation of the coughs from the stored values.

The operation of cough analyzer 80 in accordance with these example methods is described in greater detail with respect to FIGS. 6-9. In any case, the acoustic based indication may be output to processor 70, which may allow, modify, or withhold therapy based on a cough severity assessment or cough index that is derived from the acoustic signal in combination with a patient activity signal from activity sensor 84.

Although processor 70 and cough analyzer 80 are illustrated as separate modules in FIG. 3, processor 70 and cough analyzer 80 may be incorporated in a single processing unit.

Cough analyzer 80, and any of its components discussed in greater detail below, may be a component of or a module executed by processor 70.

Furthermore, the components of and functionality provided by cough analyzer 80 are described herein with respect to examples in which cough analyzer 80 is located within IMD 16. However, it is understood that any one or more cough analyzers 80 may be individually or collectively provided by any one or more devices, such as IMD 16 and programmer 24, to individually or collectively provide the functionality described herein. Programmer 24 may receive electrical signals generated by acoustic sensor 82 from IMD 16 in embodiments in which programmer 24 includes a cough analyzer.

As illustrated in FIG. 3, IMD 16 includes an activity sensor 84. Activity sensor 84 may, for example, take the form of one or more accelerometers, or any other sensor known in the art for detecting activity, e.g., body movements or footfalls, or posture. In some examples, activity sensor 84 may comprise a three-axis accelerometer. In some examples, acoustic sensor 82 and activity sensor 84 may comprise one or more common accelerometers. Processor 70 may determine an activity level count at regular intervals based on the signal(s) from activity sensor 84. In some examples, processor 70 may determine a running average activity count based on the information provided by activity sensor 84. For example, the activity count may be calculated over a 1 second interval and the processor 70 may update the activity level count at a 1 second interval. A method of determining activity count from an accelerometer sensor is described in U.S. Pat. No. 6,449,508, to Sheldon et al, entitled, "ACCELEROMETER COUNT CALCULATION FOR ACTIVITY SIGNAL FOR AN IMPLANTABLE MEDICAL DEVICE," issued Sep. 10, 2002, and incorporated herein by reference in its entirety.

Activity sensor 84 may be located outside of the housing 8 of IMD 16. Activity sensor 84 may be located in such a manner to pick up chest motion, for example. Activity sensor 84 may be located on a lead that is coupled to IMD 16 or may be implemented in a remote sensor that wirelessly communicates with IMD 16 via telemetry module 78. In any case, activity sensor 84 is electrically or wirelessly coupled to circuitry contained within housing 8 of IMD 16. As will be described in greater detail below with reference to FIGS. 6-9, processor 70 or cough analyzer 80 may use signals from activity sensor 84 in various aspects of the acoustic signal analysis.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signals, produced by sensing module 76 and/or signals by acoustic sensor 82 to programmer 24. Processor 70 may also generate and store marker codes indicative of different cardiac or other physiological events detected by sensing module 76 or cough analyzer 80, and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, the indications based on heart sounds and/or EGM signals. Such information may be included as part of a marker channel with an EGM.

Figure 4:
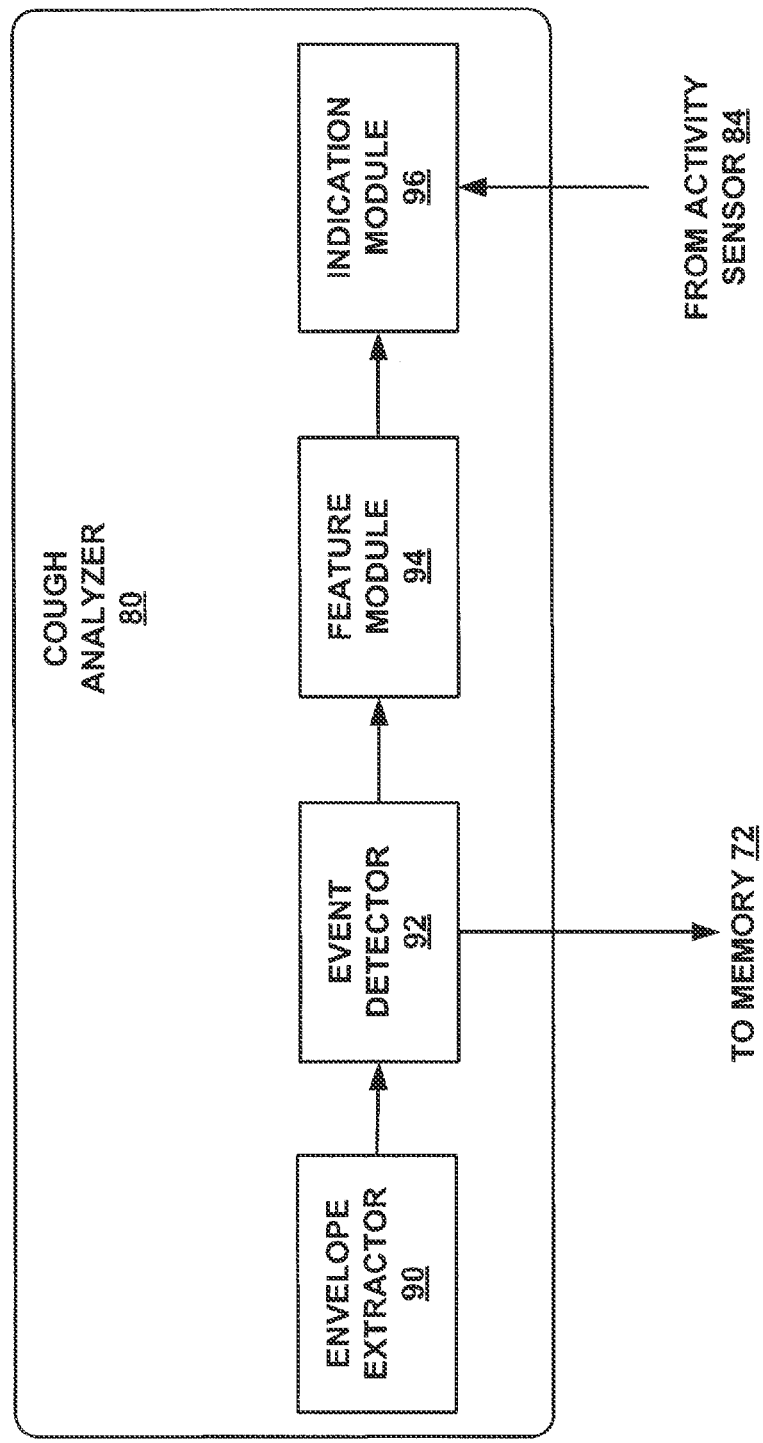
FIG. 4 is a block diagram illustrating an example configuration of the cough analyzer shown in FIG. 3.

FIG. 4 is a block diagram illustrating an example configuration of cough analyzer 80. As illustrated in FIG. 4, cough analyzer 80 may include an envelope extractor 90, event detector 92, feature module 94, and indication module 96.

Envelope extractor 90 receives an electrical signal from acoustic sensor 82. The electrical signal may be digitized and parsed into segments of predetermined length. As an example, the electrical signal generated by acoustic sensor 82 may be sampled at 256 Hertz (Hz) rate and parsed into segments including 100 or more sample points. Generally, envelope extractor 90 processes the received signal to extract an envelope, i.e., generate an envelope signal from the received signal.

In some examples envelope extractor 90 band pass filters, rectifies and smoothes the sensor signal before extracting the envelope signal. For example, envelope extractor 90 may include a high pass filter, e.g., a 40 Hz high pass filter, and a low pass filter, such as a 70 Hz low pass filter, to remove unwanted signal components from the acoustic sensor signal. In some examples a first order infinite impulse response (IIR) high pass filter with a cutoff frequency of 40 Hz and a third order IIR low pass filter with a cutoff of 70 HZ may be used. In some examples a band bass filter with a 20 Hz high pass filter and a 70 Hz low pass filter is used. In some examples, analog filtering of the acoustic sensor signal may additionally or alternatively be performed prior to digitization of the signal and receipt by envelope extractor 90. As discussed above, IMD 16 may include analog-to digital conversion circuitry.

Envelope extractor 90 may also, in some examples, include rectification circuitry and circuitry that sums the rectified signal with left-shifted and right-shifted rectified signals in order to smooth the rectified signal. In this manner, envelope extractor may approximately apply an analytic function transform to the signal for envelope extraction. In some examples, envelope extractor 90 may use other methods to generate the envelope signal, such as the normalized Shannon Energy, true Hilbert transform, or rectifying the derivative of the signal followed by moving window integration of the rectified derivative. In such examples, envelope extractor 90 extracts or generates the envelope signal of the processed signal, i.e., the band pass filtered, rectified, and smoothed signal. Extraction of the envelope signal may further include application of a box-car filter, such as a 16 point box-car filter, to the band pass filtered, rectified, and smoothed signal. Envelope extractor 90 outputs the envelope signal to heart sound event detector 92.

Event detector 92 utilizes an algorithm to detect cough events within the envelope signal. In some examples the event detector 92 also identifies heart sounds within the envelope to aid in the detection of cough events. Generally, event detector 92 identifies the local maximums of the envelope signal. In order to identify the local maximums, event detector 92 may utilize an adaptively decaying threshold. The adaptively decaying threshold may be determined based on one or more of the running average of detected heart sound and/or cough amplitudes, the running average of the envelope signal amplitude, and the mean heart sound-to-heart sound or cough-to-cough interval. Event detector 92 compares the envelope signal to the adaptively decaying threshold to identify the local maximums. Event detector 92 may store markers, referred to as "event markers," for the identified local maximums within memory 72 or provide the event markers directly to feature module 94. Feature module 94 extracts features of the detected events.

Feature module 94 may process the acoustic signal in the frequency or time domain. In some examples, feature module 94 may confirm that an event detected by event detector 92 corresponds to a cough. In some examples, feature module 94 may extract information from the acoustic signal regarding the characteristics of a cough. In some examples, feature module 94 may both confirm that an event detected by event detector 92 corresponds to a cough and extract information from the acoustic signal regarding the characteristics of the cough. In examples where the feature module 94 extracts features in the frequency domain, feature module 94 may extract features including mean or median frequency, high frequency components, low frequency components, and high/low frequency components energy ratio. In some examples where feature module 94 extracts features of the time domain, feature module 94 may extract information regarding morphology of a coughing sounds episode, duration and frequency of the sound episode or repetitiveness of coughing sounds episodes. Feature module 94 may also determine the depth of the cough.

In some examples, various features may be determined based on comparison to a template. In some examples, various features may be determined using template matching schemes that compare detected coughs to template coughs, such as a wavelet template matching scheme or a "bounded template" matching scheme. An example wavelet template matching scheme is disclosed in U.S. Pat. No. 6,393,316 issued to Jeff Gillberg. An example bounded template matching scheme is disclosed in US Publication No. 20100185109, entitled "A Blurred Template Approach for Arrhythmia Detection," by Xin Zhang, Mark Brown, Xusheng Zhang, and Jeff Gillberg.

In some examples, template coughs used for determining various cough features such as cough depth may be example coughs that are loaded into feature module 94. In some examples, template coughs may be heart sounds that were measured during a baseline interval of the patient with not cough present. That is, the template heart sounds may be obtained from patient 14 in an identified or predetermined time period during which the patient is known to have either a period without a cough present or a cough having a known profile. In some examples, memory 72 stores acoustic signals collected during coughing spells having specific characteristics as observed by the patient 14 or a physician.

In some examples, feature module 94 may load different templates depending upon information from the activity/posture sensor 84. For example, in situations where the activity sensor 84 indicates that the patient 14 is laying down the events may be compared to a different template than when patient 14 when the patient is propped up at an angle, and yet another template when the patient 14 is standing.

Indication module 96 receives information regarding various event features from feature module 94 and an activity signal from activity sensor 84. Based on the information from feature module 94 and activity sensor 84, indication module 96 may generate an indication that a cough has occurred.

In some examples, the indication of a cough is provided to processor 70. Processor 70 may update a cough index based on the indication of cough from indication module 96. In some examples, indication module 96 may also provide indication of cough severity to processor 70. The indication may be based in part on signal features including the depth of the cough. In some examples, an indication of cough severity may incorporate information from activity sensor 84. For example, an indication of a stronger cough may be made based on information from activity sensor 84 regarding chest movements.

Figure 5:
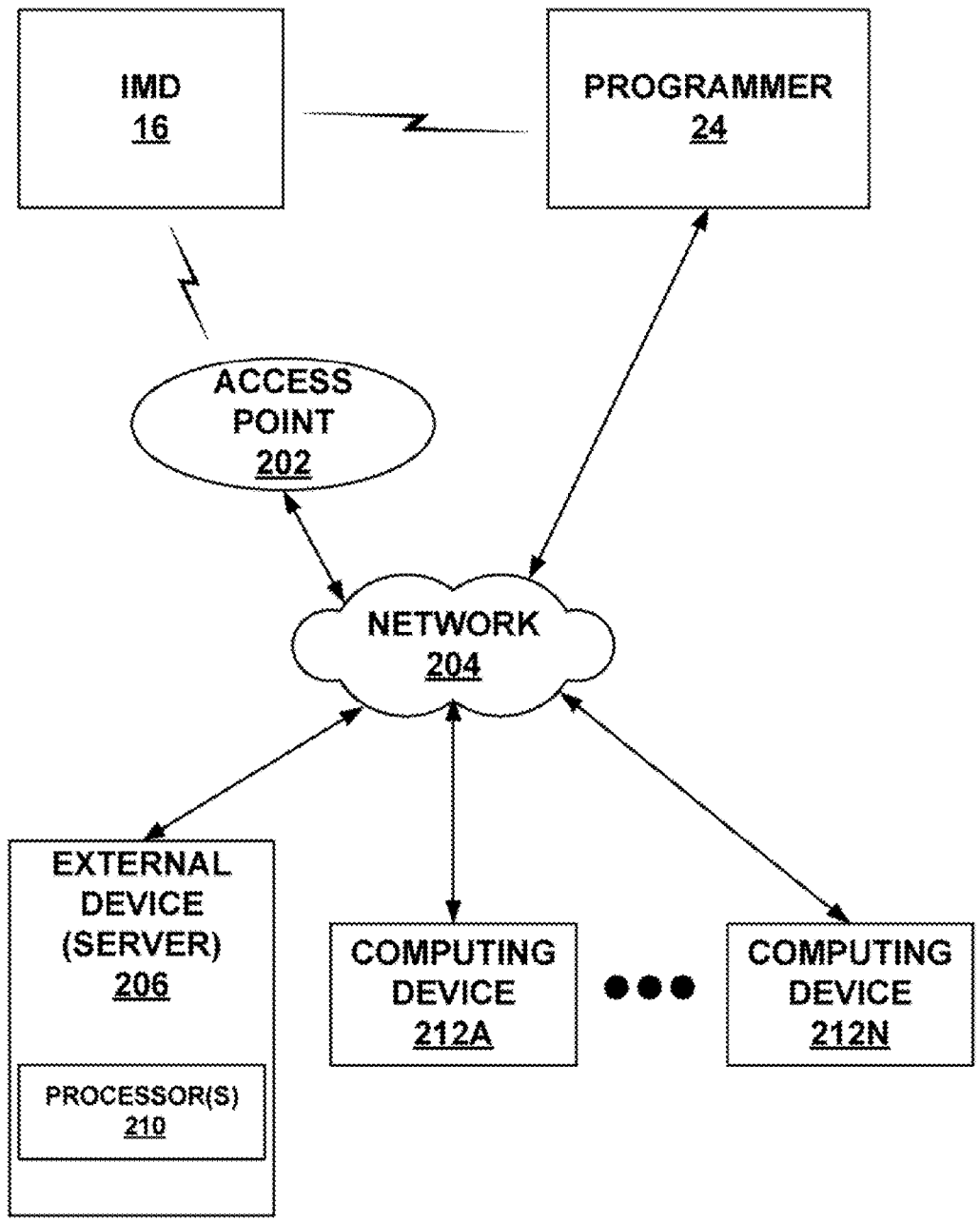
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 206, and one or more computing devices 212A-212N that are coupled to the IMD 16 and programmer 24 shown in FIG. 1 via a network 204. Network 204 may be generally used to transmit diagnostic information (e.g., the occurrence of a cough) from an IMD 16 to a remote external computing device. In some examples, the acoustic and/or EGM signals may be transmitted to an external device for processing.

In some examples, the information transmitted by IMD 16 may allow a clinician or other healthcare professional to monitor patient 14 remotely. In some examples, IMD 16 may use its telemetry module 78 to communicate with programmer 24 via a first wireless connection, and to communicate with an access point 202 via a second wireless connection, e.g., at different times. In the example of FIG. 5, access point 202, programmer 24, server 206, and computing devices 212A-212N are interconnected, and able to communicate with each other, through network 204. In some cases, one or more of access point 202, programmer 24, server 206, and computing devices 212A-3212 N may be coupled to network 204 via one or more wireless connections. IMD 16, programmer 24, server 206, and computing devices 212A-212N may each comprise one or more processors, such as one or more microprocessors, DSPs, ASICs, FPGAs, programmable logic circuitry, or the like, that may perform various functions and operations, such as those described herein.

Access point 202 may comprise a device that connects to network 204 via any of a variety of connections, such as telephone dial-up, digital subscriber line (DSL), or cable modem connections. In other examples, access point 202 may be coupled to network 204 through different forms of connections, including wired or wireless connections. In some examples, access point 202 may be co-located with patient 14 and may comprise one or more programming units and/or computing devices (e.g., one or more monitoring units) that may perform various functions and operations described herein. For example, access point 202 may include a home-monitoring unit that is co-located with patient 14 and that may monitor the activity of IMD 16. In some examples, server 206 or computing devices 212 may control or perform any of the various functions or operations described herein, e.g., determine, based on the acoustic signal, whether the patient has been coughing.

In some cases, server 206 may be configured to provide a secure storage site for archival of diagnostic information (e.g., occurrence of a coughing episode and attendant circumstances such as patient posture and activity level) that has been collected and generated from IMD 16 and/or programmer 24. Network 204 may comprise a local area network, wide area network, or global network, such as the Internet. In some cases, programmer 24 or server 206 may assemble cough information in web pages or other documents for viewing by trained professionals, such as clinicians, via viewing terminals associated with computing devices 212. The system of FIG. 5 may be implemented, in some aspects, with general network technology and functionality similar to that provided by the Medtronic CareLink® Network developed by Medtronic, Inc., of Minneapolis, Minn.

In the example of FIG. 5, external server 206 may receive acoustic information from IMD 16 via network 204. Based on the acoustic information received, processor(s) 201 may preform one or more of the functions described herein with respect to cough analyzer 80 and processor 70. In some examples, cardiac signals including EGM and heart sound (acoustic) signals are transmitted to an external device and the external device, such as server 206, processes the signals to determine whether a cough has occurred and/or provide a cough severity assessment.

Figure 6:
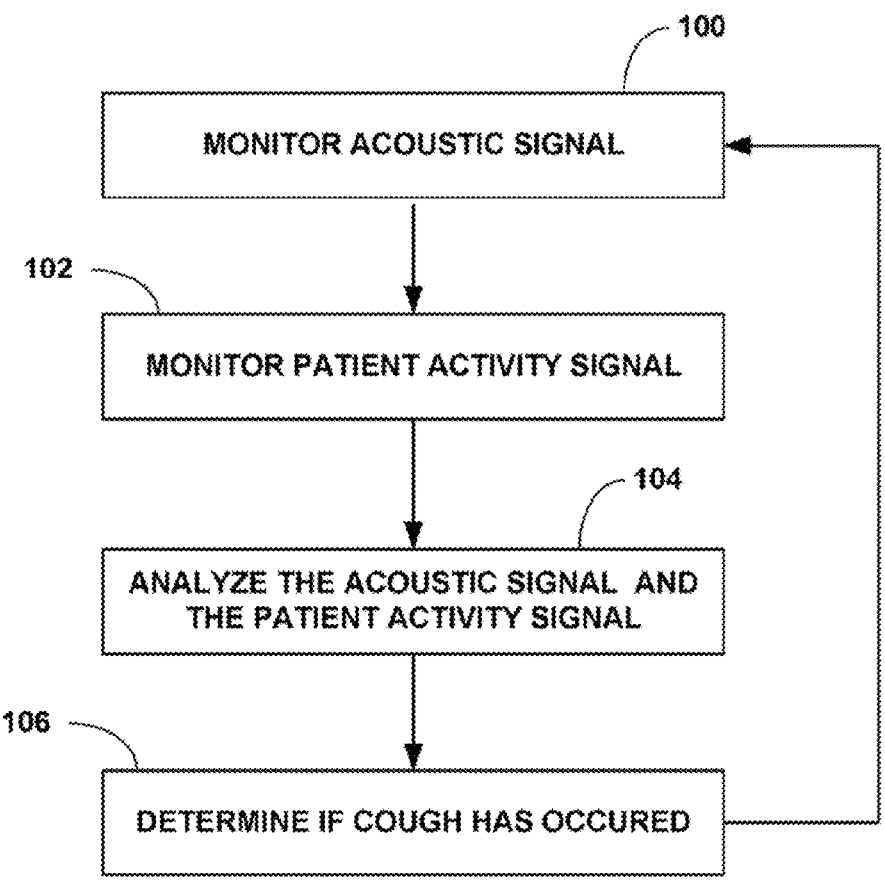
FIG. 6 is a flow diagram illustrating an example technique for detecting coughs using heart sounds.

FIG. 6 is a flow diagram illustrating an example technique for determining if a cough has occurred. Although described as being performed by IMD 16, some or all of example technique of FIG. 6 may be implemented in one or more other devices, such as programmer 24 or server 206.

IMD 16 monitors an acoustic signal (100). In some examples, acoustic sensor 82 provides the acoustic signal. Acoustic sensor 82 may be an accelerometer. In some examples, acoustic sensor 82 is positioned proximate to the diaphragm of the patient. IMD 16 also monitors a patient activity signal (102). In some examples, the patient activity signal is provided by activity sensor 84.

IMD 16 analyzes the acoustic signal and the patient activity signal (104). In some examples, the analysis may include filtering the acoustic signal. In some examples, the acoustic signal is a heart sounds signal that may be compared to a template of a heart sounds signal without a cough present in order to detect whether a cough is present. In some examples, the heart sounds signal may be compared to various templates indicating certain characteristics or types of a cough, such as a wet cough or dry cough, in order to determine characteristics or the severity of the cough.

The analysis may also include processing of the patient activity signal. In some examples, the patient activity signal may be sampled at a predetermined frequency to provide an activity count. The frequency may be every second, for example. In some examples, an activity count is a moving average of the activity level detected over a period of time. For example, the activity count may be calculated based on the average of the activity level since the last activity count was calculated.

Based on the analysis of the acoustic signal and the patient activity signal, IMD 16 determines if a cough has occurred (106). In some examples, the determination is based on the combination of information from the acoustic signal that indicates that a cough may have occurred, and activity information from the same time period, which may confirm that a cough did occur. For example, an activity signal magnitude or count greater than a predetermined threshold may indicate that a cough occurred, e.g., that the patient's chest or diaphragm moved to a degree or in a manner indicative of a cough. In some examples, the activity information, e.g., the magnitude of the activity signal or the activity count, may also help determine the severity of the cough.

Figure 7:
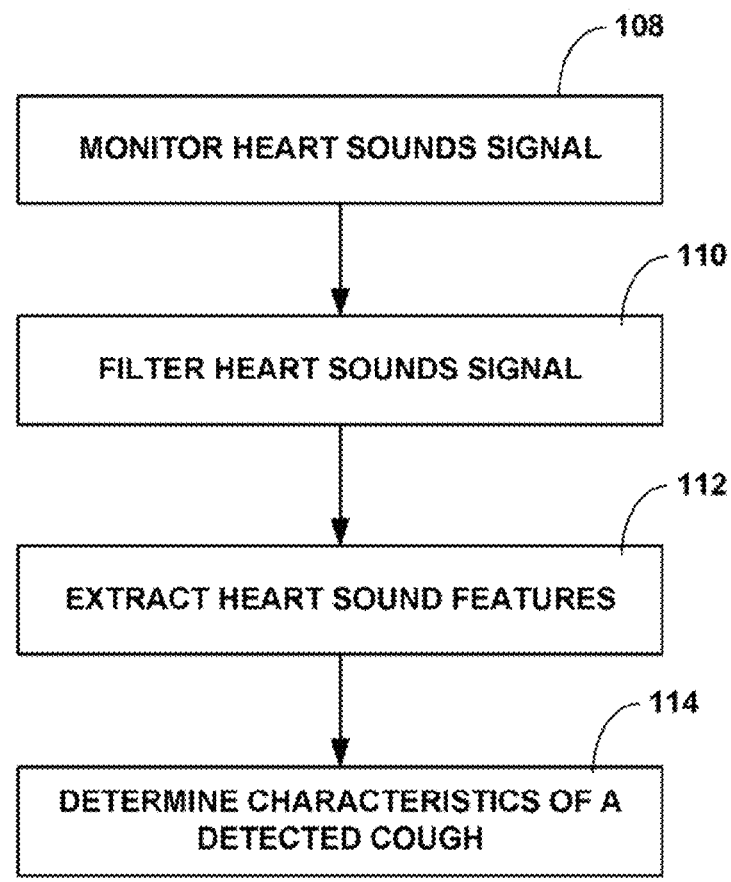
FIG. 7 is a flow diagram illustrating another example technique for detecting coughs based on heart sounds.

FIG. 7 is a flow diagram illustrating an example technique for detecting cough based on a signal including heart sounds. Although described as being performed by IMD 16, some or all of example technique of FIG. 7 may be implemented in one or more other devices, such as programmer 24 or server 206. IMD 16 monitors a heart sounds signal (108). As described above with respect to FIG. 4, IMD filters the heart sounds signal (110). IMD 16 extracts heart sound features (112) from the heart sounds signal. As discussed above with respect to FIG. 4, the features may include, for example, mean or median frequency, high and low frequency components energy ratio, and morphology of a coughing episode. Based on the extracted features, IMD 16 determines characteristics of a detected cough (114). As discussed above with respect to FIG. 4, characteristics of the detected cough may include, for example, depth of the cough, or other characteristics of the cough, e.g., a wet vs. dry cough determination, or a degree of wetness determination.

Figure 8:
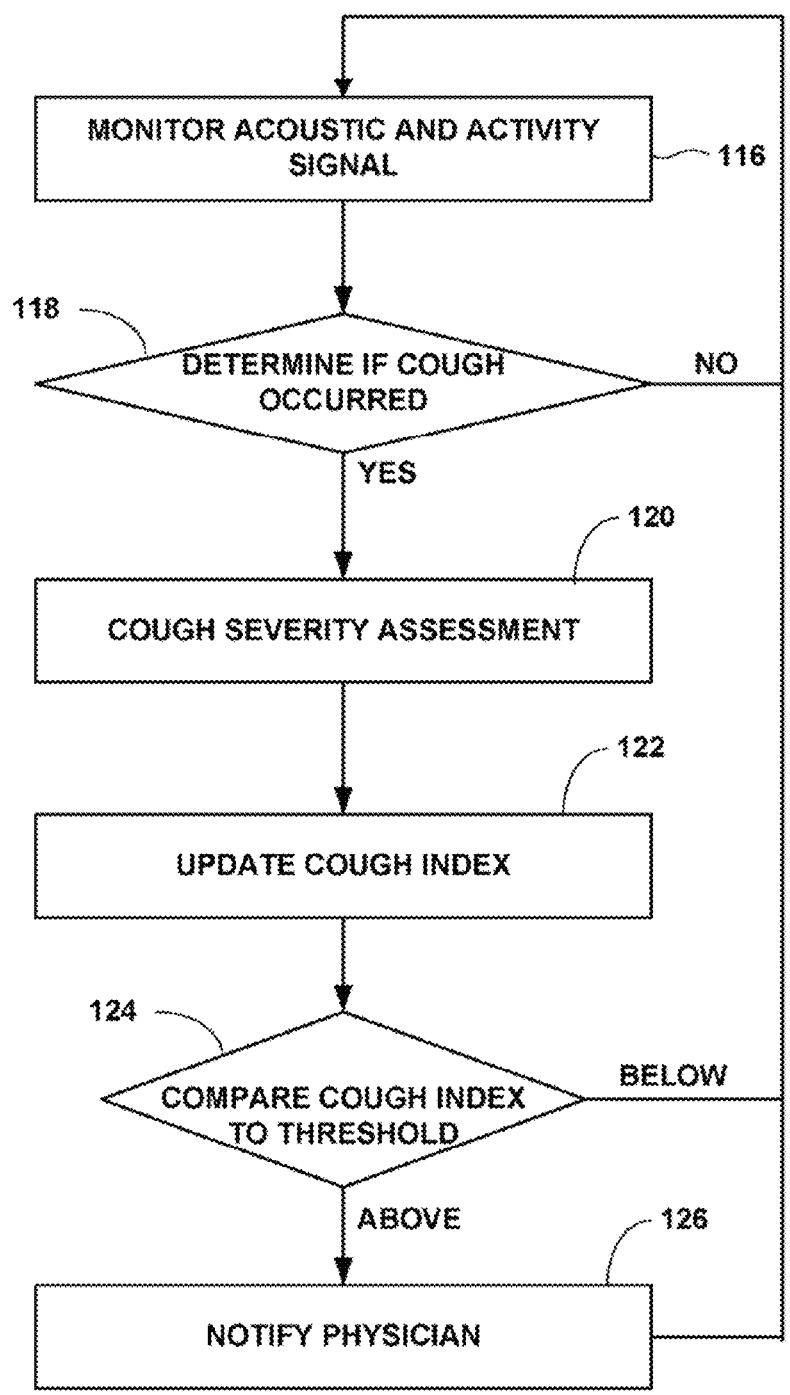
FIG. 8 is a flow diagram illustrating an example technique for detecting and categorizing a cough based at least in part on an acoustic signal.

FIG. 8 is a flow diagram illustrating an example technique for detecting and categorizing a cough based at least in part on an acoustic signal. Although described as being performed by IMD 16, some or all of example technique of FIG. 8 may be implemented in one or more other devices, such as programmer 24 or server 206.

IMD 16 monitors acoustic and activity signals (116) detected by acoustic sensor 82 and activity/posture sensor 84. Based on the monitored signals, IMD 16 determines if a cough has occurred (118). In some examples, IMD 16 determines whether a cough has occurred based on acoustic signal features such as morphology, frequency, duration, and timing. In various examples cough analyzer 80 discriminates between acoustic signals including the presence of a cough and acoustic signals including other sounds, noises, and artifacts that may have been caused by motions other than those resulting from a cough. In some examples, activity signal information, such as activity level, is used to confirm an initial determination of cough occurrence based on a heart sounds signal and extracted heart sound features. If a cough has not occurred, then IMD 16 continues to monitor acoustic and activity signals (116).

Once it has been determined if a cough has occurred (118), IMD 16 performs a cough severity assessment (120). The cough severity assessment may include, discriminating between wet and dry coughs, for example. In some examples, the cough severity assessment may include a determination of the depth of the cough. In some examples, cough severity assessment may include information regarding the frequency and/or duration of the cough. In some examples, the cough severity assessment is based on information from both the acoustic signal and the activity sensor signal.

Based on the cough assessment, IMD 16 updates a cough index (122). In some examples, processor 70 maintains and updates a cough index based on information from cough analyzer 80. In some examples, the update to the cough index (122) may be based, at least in part, on the time between the previous cough, and corresponding cough severity assessment, and the current cough, and corresponding cough severity assessment.

For example, a cough index may be incremented based on the occurrence of a cough. The amount that the cough index is incremented may be determined based on the severity of the cough, e.g., the cough index may be incremented by a greater amount if the cough is more severe. In some examples, the cough index may be decremented based on the passage of a predetermined amount of time without the detection of a cough. After the cough index is updated, the cough index is compared to a threshold (124).

In some examples, the processor 70 may compare the cough index to a plurality of predetermined thresholds. In some examples, the thresholds may be chosen by a physician. Each threshold may be associated with a different response by the processor. For example, processor 70 may notify a physician (126) of the cough index level when a first threshold has been passed. The notification to the physician may include an indication that the risk of a heart failure event, e.g., decompensation and/or hospitalization, or arrhythmia for the patient has increased. In some examples, telemetry module 78 communicates with a remote device to provide an indication that the threshold has been passed.

In some examples, in response to a second threshold, processor 70 may modify the cardiac stimulation being provided to the heart 14. In some examples, one or more of the predetermined thresholds is set to flag a change in heart failure status. In such examples, processor 70 may modify cardiac resynchronization therapy parameters to combat the decline in heart function. In some examples, the physician may review and modify therapy parameters in response to the notification.

In some examples, the coughing index may be considered in conjunction with other physiological parameters or indices derived from other physiological parameters when assessing the progression of heart failure or efficacy of cardiac resynchronization therapy. For example, the coughing index may be considered in conjunction with thoracic impedance, or a thoracic edema or fluid index derived from thoracic impedance, such as that provided by Optivol® feature of certain IMDs available from Medtronic, Inc. of Minneapolis, Minn. In some examples, the coughing index may additionally or alternatively be considered in conjunction with one or more of heart rate variability, night heart rate, respiration depth or frequency, activity, or arrhythmia burden, as examples.

Figure 9:
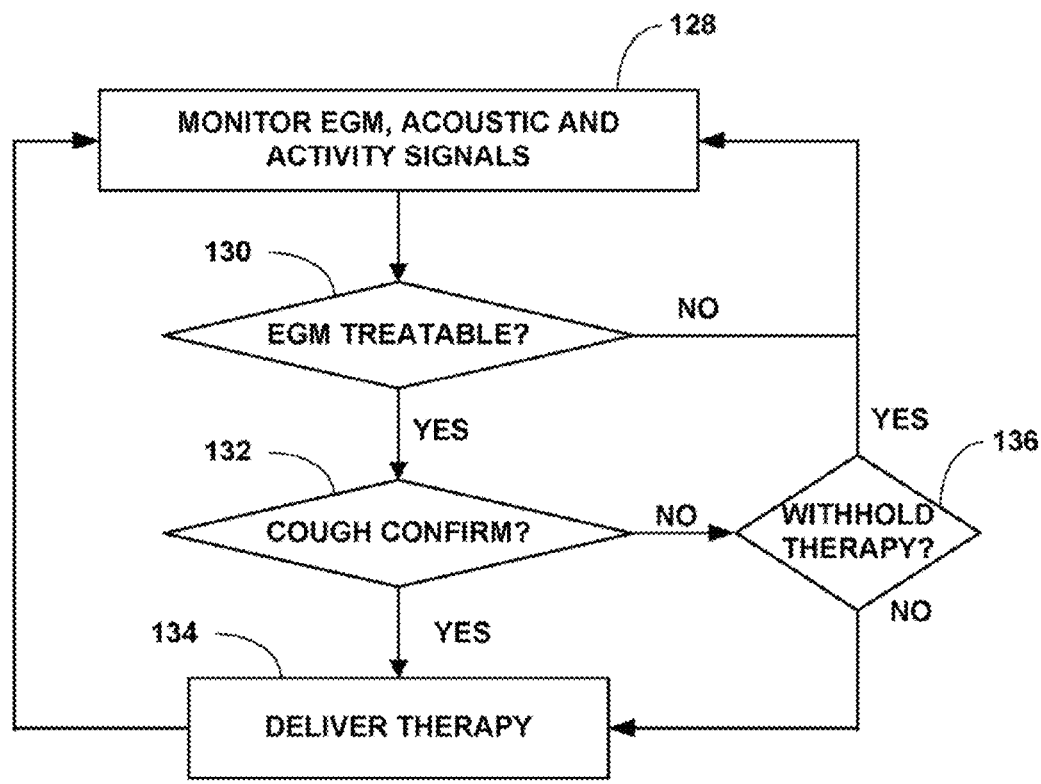
FIG. 9 is a flow diagram illustrating an example technique for arrhythmia detection.

FIG. 9 illustrates an example technique for confirming the presence of various arrhythmias using cough detection. In some examples, the presence of a cough is used to help confirm the presence of ventricular tachycardia or ventricular fibrillation.

IMD 16 monitors EGM, acoustic, and activity signals (128). In some examples, the EGM signal is monitored by sensing module 76, the acoustic signal is monitored by acoustic sensor 82, and the activity signal is monitored by activity/posture sensor 84. When a possible arrhythmia is detected in the EGM signal, processor 70 determines if the abnormal EGM includes a treatable arrhythmia (130). If processor 70 determines that the arrhythmia is not treatable with the stimulation available, then IMD 16 continues to monitor the various signals. In some examples, an indication of the abnormal EGM is also provided to a remote device via telemetry module 76. In some examples, the presence of a cough is used to confirm (132) the presence of an arrhythmia. The determination of the presence of a cough is based on the acoustic and activity signals. In some examples, the cough based confirmation (132) may be based on the cough index. For example, if the cough index is above a predetermined level, then the arrhythmia is confirmed, and therapy is delivered (134). After therapy is delivered, IMD 16 continues to monitor EGM, acoustic and activity signals. In some examples, IMD 16 may perform additional confirmation checks before making the determination of whether to deliver therapy or not. For example, other aspects of the acoustic signal may be used to confirm the presence of an arrhythmia, or the appropriateness of the chosen treatment. In some examples, IMD 16 may decide whether or not to withhold therapy (136) based at least in part on the cough confirmation.

Figure 10:
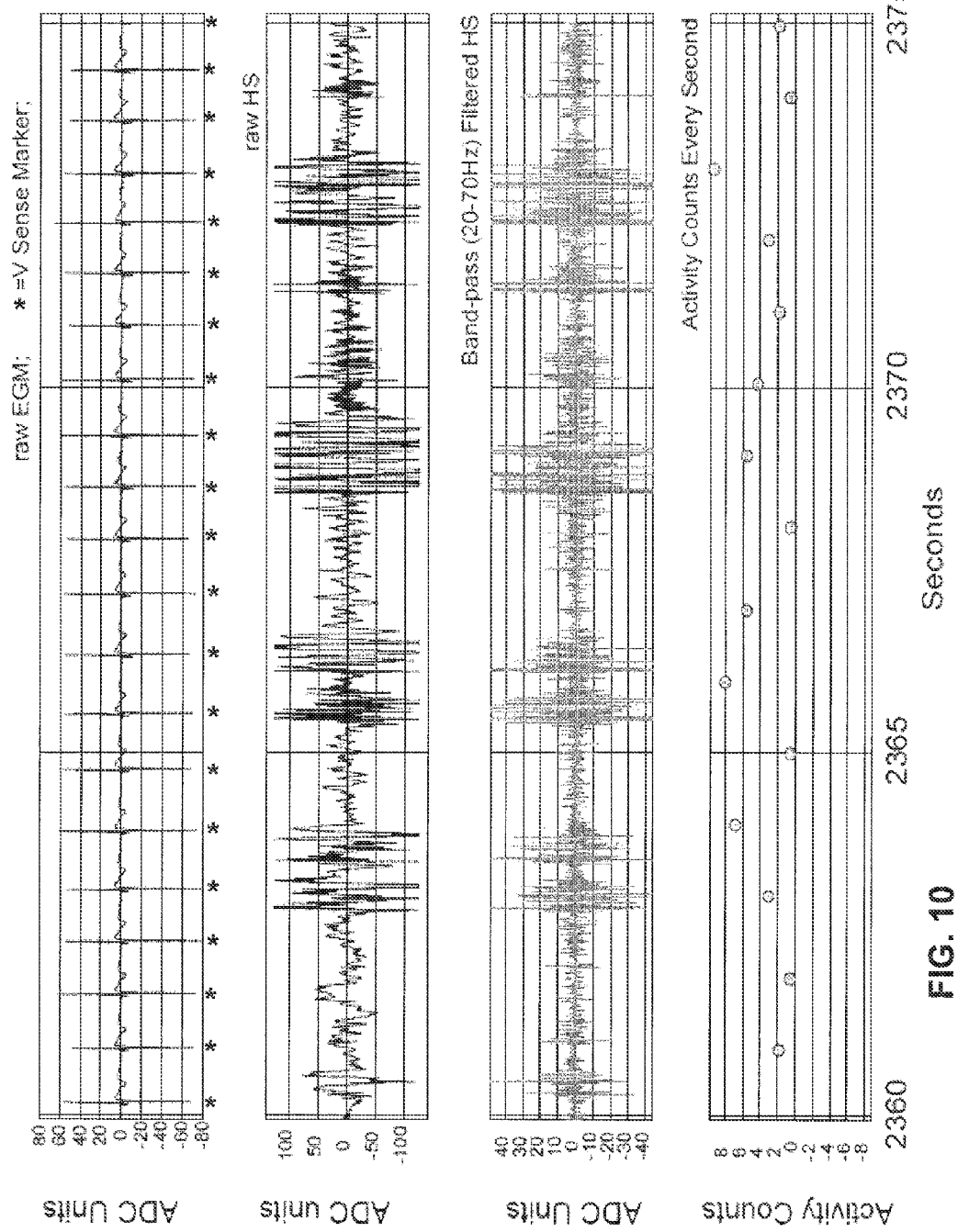
FIG. 10 illustrates a heart sounds signal indicating the presence of a cough.

FIG. 10 illustrates example waveforms detected by IMD 16. EGM signal 140 may be collected by sensing module 74. The EGM signal 140 may be processed by sensing module 74 or by processor 70, for example. In some examples, IMD 16 monitors EGM signal 140 to determine whether an arrhythmia has occurred. Heart sounds signal 150 may be collected by acoustic sensor 82. A determination of whether a cough has occurred is based at least in part on information extracted from heart sounds signal 150. In some examples, heart sounds signal 150 is filtered, resulting in filtered heart sounds signal 160. The filtered heart sounds signal 160 is used, along with activity count 170, to determine whether a cough has occurred. Filtered heart sounds signal 160 is a filtered heart sounds signal during a coughing episode. In some examples, an activity count above certain level indicates that a cough is occurring. In some examples, the activity count is above 4 when coughing occurs.

Figure 11:
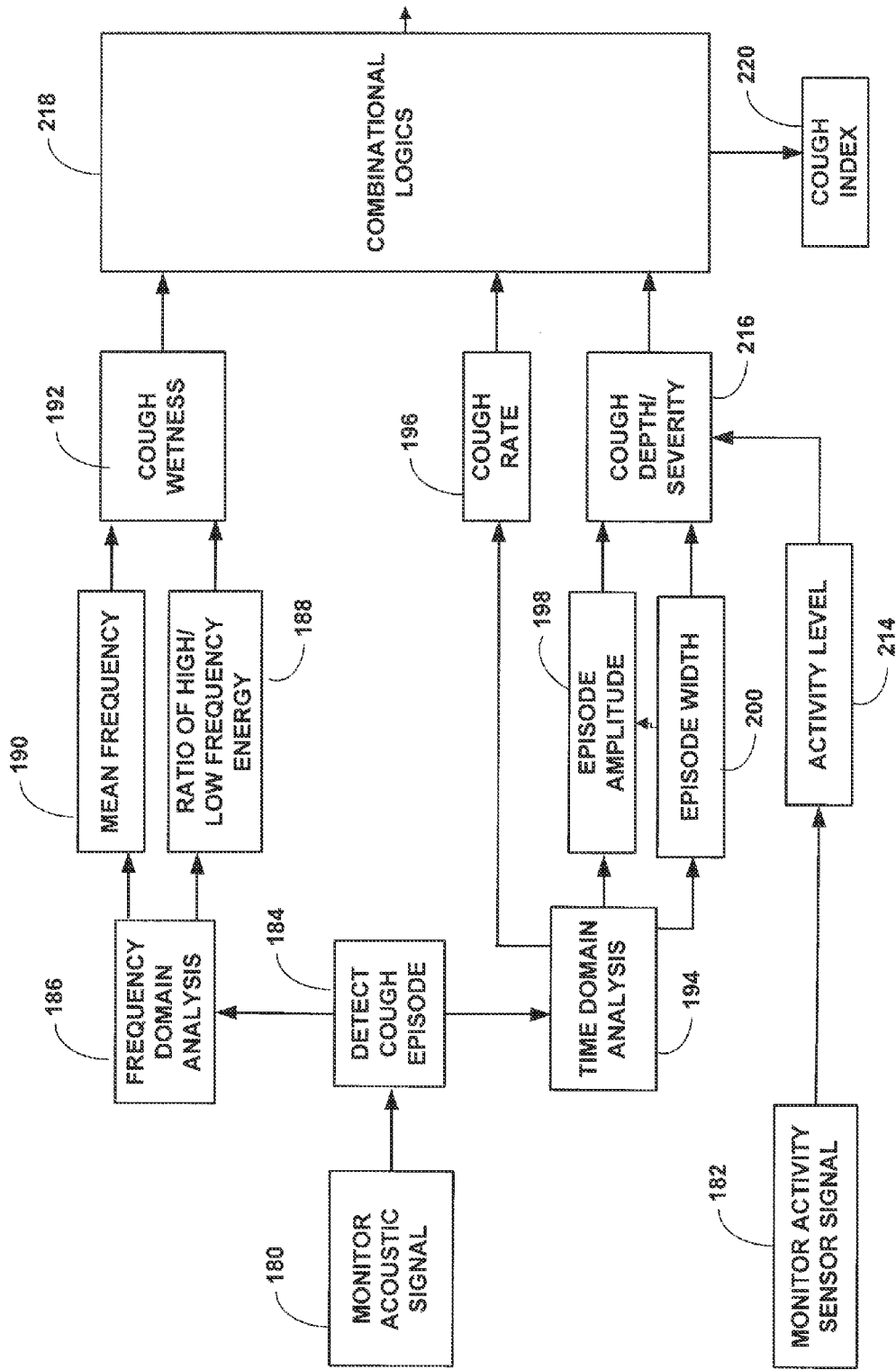
FIG. 11 is a flow diagram illustrating an example technique for updating a cough index.

FIG. 11 is a flow diagram illustrating an example technique for updating a cough index. Although described as being performed by IMD 16, some or all of example technique of FIG. 11 may be implemented in one or more other devices, such as programmer 24 or server 206. IMD 16 monitors an acoustic signal (180) from acoustic sensor 82. IMD 16 also monitors an activity sensor signal (182) from activity sensor 84. Based on the activity sensor signal processor 70 may determine an activity level (214). Based on at least the monitored acoustic signal, IMD 16 detects a cough episode (184). In some examples, detection of a cough episode (184) is performed as described above with respect to FIG. 6. In response to the detecting a cough episode the IMD performs one or both of a frequency domain analysis (186) and time domain analysis (194) of the acoustic signal. In some examples the analysis may be performed by cough analyzer 80.

Frequency domain analysis (186) may include, for example, determination of the mean frequency (190) of the acoustic signal, as well a ratio of, or other metric comparing or based on, high and low frequency energy (188). In some examples, cough analyzer 80, and in particular features module 94, may perform some or all of the frequency domain analysis (186). The mean frequency (190), as well as the ratio of high to low frequency energy (188), may be determined based on acoustic signal samples obtained during a predetermined period of time or window. In some examples, the predetermined period of time is a rolling one minute window.

In some examples, the mean frequency may be determined for a cough episode including a plurality of coughs. In some examples a cough episode is a single cough. Based on the mean frequency (190) and ratio of high to low frequency energy (180) for the cough episode, cough wetness (192) may be determined. In some examples, the cough wetness is on a 0.0 to 1.0 scale with 0.0 being extremely dry, and 1.0 being extremely wet.

Time domain analysis (194) may include a determination of cough rate (196). In some examples, the cough rate (196) is determined as the number of coughs per unit time, such as per minute. In some examples, the cough rate is frequently updated based on a number of coughs detected within a rolling one minute window of acoustic signal data. In some examples, cough analyzer 80 may determine an episode amplitude (198) as well as episode width (200).

In some examples, the cough analyzer 80 determines an amplitude and width for each cough that occurs within a one minute window. Cough depth and/or severity (216) may be determined based on one or more of episode amplitude (198), episode width (200) and activity level (214). One example measure of cough severity and depth may be based on an average of the amplitudes for each cough that occurred during a predetermined time window. Another measure of cough depth and severity may take into consideration the average width (length of time) of each cough within the predetermined time window, as well as the activity level. In some examples, the activity level may be an indication of how far the chest was displaced as a result of the cough. The cough depth and severity may be on a scale. For example, the cough depth and severity (216) assessment may result in a value on a 0.0 to 1.0 scale. In other examples, the scale may be from 0.0 to 10.0.

The cough index (220) may be determined based on one the cough wetness (192), the cough rate (196) and the cough depth and severity (216). In some examples, combinational logics (218) may multiply the value of the cough wetness (192), the cough rate (196) and the value of the cough depth and severity (216). As described above, the cough wetness (192), the cough rate (196) and the cough depth and severity may be numerical values, e.g., between 0.0 and 1.0. The resulting value may be the cough index (220).

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples have been described. These and other examples are within the scope of the following claims.

The invention claimed is:

1. A method comprising:
   receiving an acoustic signal from an acoustic sensor implanted in a patient;
   receiving a patient activity signal from an activity sensor implanted in the patient;
   analyzing the acoustic signal in combination with the patient activity signal;
   determining whether a cough has occurred based on the analysis of the acoustic signal in combination with the patient activity signal;
   determining a severity of the cough based on the analysis of the acoustic signal and the patient activity signal; and
   incrementing a cough index by an amount that is determined based on the severity of the cough.

2. The method of claim 1, wherein determining a severity of the cough comprises determining a duration and frequency of a cough episode.

3. The method of claim 1, wherein determining a severity of the cough comprises determining an amplitude of the cough.

4. The method of claim 1, further comprising determining a depth of the cough based on one or more of the acoustic signal and the patient activity signal.

5. The method of claim 1, further comprising determining if the cough is a wet cough based on the acoustic signal.

6. The method of claim 1, further comprising sending a notification when the cough index passes a predetermined threshold.

7. The method of claim 1, further comprising providing therapy in response to the cough index passing a predetermined threshold.

8. The method of claim 1, wherein the acoustic signal is detected using a first accelerometer and the patient activity signal is detected using a second accelerometer.

9. The method of claim 1, further comprising determining, based on the incremented cough index, whether heart failure has worsened in the patient.

10. The method of claim 1, further comprising determining, based on the incremented cough index, a ventricular tachycardia or ventricular fibrillation risk.

11. The method of claim 1, wherein the acoustic signal is detected using a piezoelectric sensor.

12. The method of claim 1, wherein the determination of whether a cough has occurred comprises filtering the acoustic signal and determining a patient activity level based on the patient activity signal.

13. The method of claim 1, wherein the acoustic signal includes one or more heart sounds.

14. A system comprising:
   a cough analyzer configured to:
      receive an acoustic signal from an acoustic sensor,
      receive a patient activity signal from an activity sensor, and
      analyze the acoustic signal in combination with the patient activity signal; and
   a processor configured to:
   determine whether a cough has occurred based on the analysis of the acoustic signal in combination with the patient activity signal;
   provide a cough severity assessment based on the analysis of the acoustic signal in combination with the patient activity signal; and
   increment a cough index by an amount that is determined based on the severity of the cough.

15. The system of claim 14, wherein the cough analyzer is further configured to determine a duration and frequency of cough sound episodes based on the acoustic signal.

16. The system of claim 14, wherein the cough analyzer is further configured to determine an amplitude of a cough based on the acoustic signal.

17. The system of claim 14, wherein the cough analyzer is further configured to determine a depth of the cough based on one or more of the acoustic signal and the patient activity signal.

18. The system of claim 14, wherein the cough analyzer is further configured to determine if the cough is a wet cough or a dry cough based on the acoustic signal.

19. The system of claim 14, wherein the processor is further configured to send a notification when the cough index passes a predetermined threshold.

20. The system of claim 19, further including a telemetry module configured to send the notification to a remote device.

21. The system of claim 19, further including a signal generator configured to provide therapy in response to the cough index passing a predetermined threshold.

22. The system of claim 14, wherein the acoustic sensor is a first accelerometer and the activity sensor is a second accelerometer.

23. The system of claim 14, wherein the processor is further configured to determine, based on the incremented cough index, whether heart failure has worsened in a patient.

24. The system of claim 14, wherein the processor is further configured to determine, based on the incremented cough index, a ventricular tachycardia or ventricular fibrillation risk.

25. The system of claim 14, further comprising an implantable medical device comprising a housing that houses the acoustic sensor, the activity sensor and the processor.

26. The system of claim 25, wherein the implantable medical device is configured to perform at least one of
   monitoring a cardiac electrical signal; and
   delivering therapeutic electrical signals to a heart.

27. The system of claim 14, wherein the acoustic sensor comprises a piezoelectric sensor.

28. The system of claim 14, wherein the acoustic sensor is a heart sounds sensor.

29. A system comprising:
- means for receiving an acoustic signal from an acoustic sensor;
- means for receiving a patient activity signal from an activity sensor;
- means for analyzing the acoustic signal in combination with the patient activity signal;
- means for determining whether a cough has occurred based on the analysis of the acoustic signal in combination with the patient activity signal;
- means for analyzing the acoustic signal and the patient activity signal to provide a cough severity assessment; and
- means for incrementing a cough index by an amount that is determined based on the severity of the cough.

\* \* \* \* \*